(12) United States Patent
Marnfeldt et al.

(10) Patent No.: US 9,814,882 B2
(45) Date of Patent: **\*Nov. 14, 2017**

(54) RECHARGEABLE-BATTERY IMPLANTABLE MEDICAL DEVICE HAVING A PRIMARY BATTERY ACTIVE DURING A RECHARGEABLE-BATTERY UNDERVOLTAGE CONDITION

(71) Applicant: Boston Scientific Neuromodulation Corporation, Valencia, CA (US)

(72) Inventors: Goran N. Marnfeldt, Valencia, CA (US); Rafael Carbunaru, Valley Village, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/149,791

(22) Filed: May 9, 2016

(65) Prior Publication Data

US 2016/0250475 A1    Sep. 1, 2016

Related U.S. Application Data

(63) Continuation of application No. 14/599,735, filed on Jan. 19, 2015, now Pat. No. 9,345,883.

(Continued)

(51) Int. Cl.
*A61N 1/00* (2006.01)
*A61N 1/36* (2006.01)
(Continued)

(52) U.S. Cl.
CPC ....... *A61N 1/36125* (2013.01); *A61N 1/3787* (2013.01); *H02J 7/00* (2013.01);
(Continued)

(58) Field of Classification Search
CPC ... A61N 1/36125; A61N 1/3787; A61N 1/378
See application file for complete search history.

(56) References Cited

U.S. PATENT DOCUMENTS

| | | |
|---|---|---|
| 3,522,811 A | 8/1970 | Wingrove et al. |
| 3,867,950 A | 2/1975 | Fischell |
| | (Continued) | |

FOREIGN PATENT DOCUMENTS

| | | |
|---|---|---|
| JP | 06-125994 | 5/1994 |
| JP | 2000122811 | 4/2000 |
| | (Continued) | |

OTHER PUBLICATIONS

Data Sheet for Motorola Device No. MC33349, "Lithium Battery Protection Circuit for One Cell Battery Packs," (May 2000).

*Primary Examiner* — Robert N Wieland
(74) *Attorney, Agent, or Firm* — Lewis, Reese & Nesmith, PLLC

(57) ABSTRACT

A rechargeable-battery Implantable Medical Device (IMD) is disclosed including a primary battery which can be used as a back up to power critical loads in the IMD when the rechargeable battery is undervoltage and other non-critical loads are thus decoupled from the rechargeable battery. A rechargeable battery undervoltage detector provides at least one rechargeable battery undervoltage control signal to a power supply selector, which is used to set the power supply for the critical loads either to the rechargeable battery voltage when the rechargeable battery is not undervoltage, or to the primary battery voltage when the rechargeable battery is undervoltage. Circuitry for detecting the rechargeable battery undervoltage condition may be included as part of the critical loads, and so the undervoltage control signal(s) is reliably generated in a manner to additionally (Continued)

decouple the rechargeable battery from the load to prevent further rechargeable battery depletion.

19 Claims, 8 Drawing Sheets

Related U.S. Application Data

(60) Provisional application No. 61/940,272, filed on Feb. 14, 2014.

(51) Int. Cl.

| *A61N 1/378* | (2006.01) |
| *H02J 7/00* | (2006.01) |
| *H02J 7/02* | (2016.01) |
| *H02J 50/10* | (2016.01) |
| *A61N 1/37* | (2006.01) |

(52) U.S. Cl.
CPC .......... *H02J 7/0024* (2013.01); *H02J 7/0063* (2013.01); *H02J 7/025* (2013.01); *H02J 50/10* (2016.02); *A61N 1/3708* (2013.01); *H02J 7/0031* (2013.01); *H02J 2007/0067* (2013.01)

(56) References Cited

U.S. PATENT DOCUMENTS

| 3,888,260 | A | 6/1975 | Fischell |
| 3,942,535 | A | 3/1976 | Schulman |
| 4,082,097 | A | 4/1978 | Mann et al. |
| 4,096,866 | A | 6/1978 | Fischell |
| 4,408,607 | A | 10/1983 | Maurer |
| 4,548,209 | A | 10/1985 | Wielders et al. |
| 4,556,061 | A | 12/1985 | Barreras et al. |
| 4,599,523 | A | 7/1986 | Pless et al. |
| 4,793,353 | A | 12/1988 | Borkan |
| 4,947,844 | A | 8/1990 | McDermott |
| 5,080,096 | A | 1/1992 | Hooper et al. |
| 5,222,494 | A | 6/1993 | Baker, Jr. |
| 5,235,979 | A | 8/1993 | Adams |
| 5,312,439 | A | 5/1994 | Loeb |
| 5,314,458 | A | 5/1994 | Najafi et al. |
| 5,391,193 | A | 2/1995 | Thompson |
| 5,411,357 | A | 5/1995 | Munshi et al. |
| 5,557,210 | A | 9/1996 | Cappa et al. |
| 5,584,883 | A | 12/1996 | Rauch et al. |
| 5,591,212 | A | 1/1997 | Keimel |
| 5,602,460 | A | 2/1997 | Fernandez et al. |
| 5,650,974 | A | 7/1997 | Yoshimura |
| 5,679,022 | A | 10/1997 | Cappa et al. |
| 5,702,431 | A | 12/1997 | Wang et al. |
| 5,713,939 | A | 2/1998 | Nedungadi et al. |
| 5,733,313 | A | 3/1998 | Barreras et al. |
| 5,769,877 | A | 6/1998 | Barreras et al. |
| 5,807,397 | A | 9/1998 | Barreras et al. |
| 5,869,970 | A | 2/1999 | Palm et al. |
| 5,904,705 | A | 5/1999 | Kroll et al. |
| 5,925,068 | A | 7/1999 | Kroll |
| 6,067,474 | A | 5/2000 | Schulman et al. |
| 6,164,284 | A | 12/2000 | Schulman et al. |
| 6,185,452 | B1 | 2/2001 | Schulman et al. |
| 6,208,894 | B1 | 3/2001 | Schulman et al. |
| 6,272,382 | B1 | 8/2001 | Faltys et al. |
| 6,308,101 | B1 | 10/2001 | Faltys et al. |
| 6,350,263 | B1 | 2/2002 | Wetzig et al. |
| 6,381,496 | B1 | 4/2002 | Meadows et al. |
| 6,393,325 | B1 | 5/2002 | Mann et al. |
| 6,507,173 | B1 | 1/2003 | Spiridon et al. |
| 6,516,227 | B1 | 2/2003 | Meadows et al. |
| 6,553,262 | B1 | 4/2003 | Lang et al. |
| 6,553,263 | B1 | 4/2003 | Meadows et al. |
| 6,650,942 | B2 | 11/2003 | Howard et al. |
| 6,757,566 | B2 | 6/2004 | Weiner et al. |
| 6,778,856 | B2 | 8/2004 | Connelly et al. |
| 6,826,430 | B2 | 11/2004 | Faltys et al. |
| 6,894,456 | B2 | 5/2005 | Tsukamoto |
| 6,920,359 | B2 | 7/2005 | Meadows et al. |
| 7,012,405 | B2 | 3/2006 | Nishida et al. |
| 7,079,893 | B2 | 7/2006 | Greatbatch et al. |
| 7,177,691 | B2 | 2/2007 | Meadows et al. |
| 7,177,698 | B2 | 2/2007 | Klosterman et al. |
| 7,184,836 | B1 | 2/2007 | Meadows et al. |
| 7,209,784 | B2 | 4/2007 | Schmidt |
| 7,212,110 | B1 | 5/2007 | Martin et al. |
| 7,248,929 | B2 | 7/2007 | Meadows et al. |
| 7,295,878 | B1 | 11/2007 | Meadows et al. |
| 7,337,001 | B2 | 2/2008 | Schmidt |
| 7,428,438 | B2 | 9/2008 | Parramon et al. |
| 7,437,193 | B2 | 10/2008 | Parramon et al. |
| 7,482,438 | B2 | 1/2009 | Eliu et al. |
| 7,528,582 | B1 | 5/2009 | Ferguson |
| 7,545,398 | B2 | 6/2009 | Sawada |
| 7,565,204 | B2 | 7/2009 | Matei |
| 7,657,315 | B2 | 2/2010 | Schmidt |
| 7,720,546 | B2 | 5/2010 | Ginggen et al. |
| 7,773,581 | B2 | 6/2010 | Spurlin et al. |
| 7,801,600 | B1 | 9/2010 | Carbunaru |
| 7,801,615 | B2 | 9/2010 | Meadows et al. |
| 7,822,480 | B2 | 10/2010 | Park et al. |
| 7,840,279 | B2 | 11/2010 | He |
| 7,962,222 | B2 | 6/2011 | He et al. |
| 8,027,728 | B2 | 9/2011 | Schmidt et al. |
| 8,175,717 | B2 | 5/2012 | Haller et al. |
| 8,185,212 | B2 | 5/2012 | Carbunaru et al. |
| 8,305,052 | B2 | 11/2012 | Batikoff et al. |
| 8,386,048 | B2 | 2/2013 | McClure et al. |
| 8,401,659 | B2 | 3/2013 | Von Arx et al. |
| 8,423,132 | B2 | 4/2013 | Vaingast et al. |
| 8,478,404 | B2 | 7/2013 | Maile et al. |
| 8,577,474 | B2 | 11/2013 | Rahman et al. |
| 8,606,362 | B2 | 12/2013 | He et al. |
| 8,676,318 | B2 | 3/2014 | Carbunaru et al. |
| 2002/0133211 | A1 | 9/2002 | Weiner et al. |
| 2003/0191504 | A1 | 10/2003 | Meadows et al. |
| 2003/0195581 | A1 | 10/2003 | Meadows et al. |
| 2004/0217734 | A1 | 11/2004 | Shum |
| 2005/0131495 | A1 | 6/2005 | Parramon et al. |
| 2007/0060980 | A1 | 3/2007 | Strother et al. |
| 2007/0150019 | A1* | 6/2007 | Youker ............ A61N 1/3787 607/29 |
| 2007/0270922 | A1 | 11/2007 | Zierhofer et al. |
| 2011/0276110 | A1 | 11/2011 | Whitehurst et al. |
| 2013/0023943 | A1 | 1/2013 | Parramon et al. |
| 2014/0249603 | A1 | 9/2014 | Yan et al. |

FOREIGN PATENT DOCUMENTS

| JP | 2001-322515 | 11/2001 |
| JP | 2002201321 | 7/2002 |

\* cited by examiner

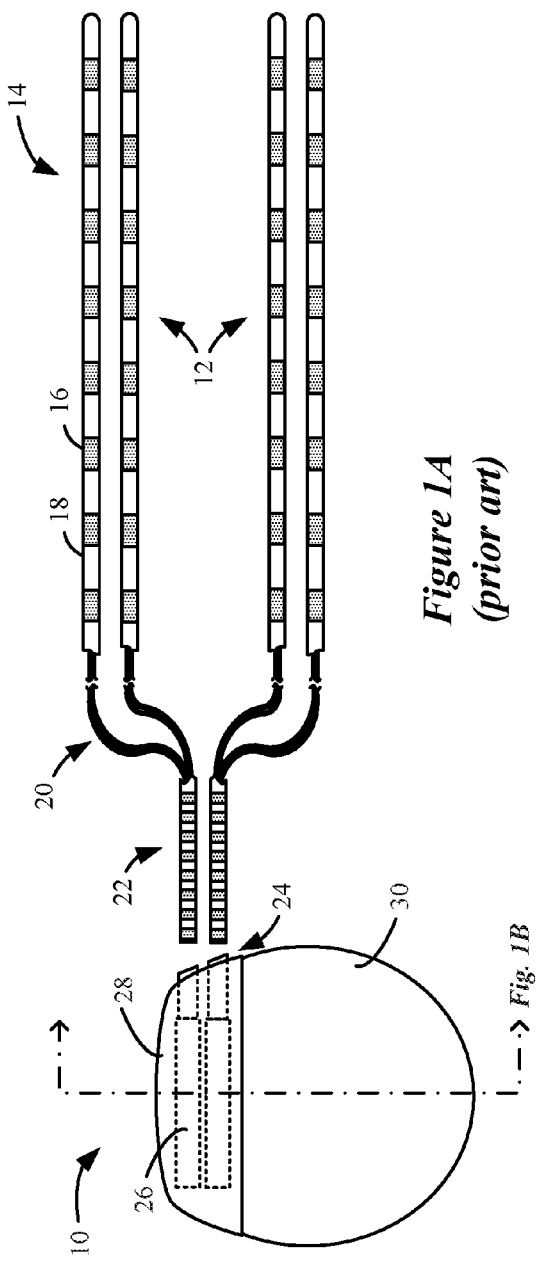
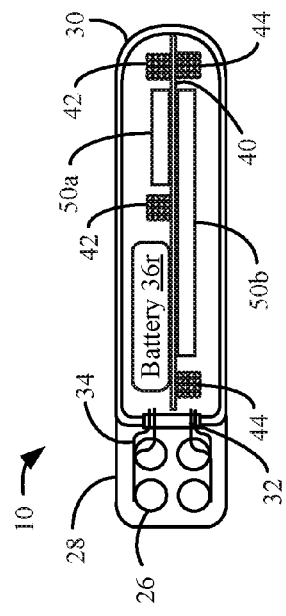
*Figure 1A (prior art)*
*Figure 1B (prior art)*

RECHARGEABLE-BATTERY IMPLANTABLE MEDICAL DEVICE HAVING A PRIMARY BATTERY ACTIVE DURING A RECHARGEABLE-BATTERY UNDERVOLTAGE CONDITION

CROSS REFERENCE TO RELATED APPLICATIONS

This is a continuation of U.S. Non-Provisional patent application Ser. No. 14/599,735, filed Jan. 19, 2015 (now U.S. Pat. No. 9,345,883), which is a Non-Provisional of U.S. Provisional Patent Application Ser. No. 61/940,272, filed Feb. 14, 2014. Priority is claimed to these applications, and they are incorporated herein by reference in their entireties.

FIELD OF THE INVENTION

This application relates to the field of implantable medical devices, and in particular to batteries useable in an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical.

An SCS system typically includes an Implantable Pulse Generator (IPG) 10 shown in plan and cross-sectional views in FIGS. 1A and 1B. The IPG 10 includes a biocompatible device case 30 that holds the circuitry and battery 36 necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26, which are in turn coupled by feedthrough pins 34 through a case feedthrough 32 to circuitry within the case 30.

In the illustrated IPG 10, there are thirty-two lead electrodes (E1-E32) split between four leads 14, with the header 28 containing a 2×2 array of lead connectors 24. However, the number of leads and electrodes in an IPG is application specific and therefore can vary. In a SCS application, the electrode leads 14 are typically implanted proximate to the dura in a patient's spinal cord, and when a four-lead IPG 10 is used, these leads are usually split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IPG 10 can also be used for Deep Brain Stimulation (DBS) in another example. In other IPG examples designed for implantation directly at a site requiring stimulation, the IPG can be lead-less, having electrodes 16 instead appearing on the body of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable (36*r*); other circuitry 50*a* and 50*b* coupled to top and bottom surfaces of the PCB; a telemetry coil 42 for wirelessly communicating with an external controller (not shown); a charging coil 44 for wirelessly receiving a magnetic charging field from an external charger 90 (FIG. 2) for recharging the battery 36; and the feedthrough pins 34 (connection not shown). (Further details concerning operation of the coils 42 and 44 and the external devices with which they communicate can be found in U.S. Patent Application Publication 2015/0080982.

An issue requiring care in an IPG 10, especially one in which the battery 36 is rechargeable, is design of the battery management circuitry, which is described in one example in commonly-owned U.S. Patent Application Publication 2013/0023943, which is incorporated herein by reference in its entirety. FIG. 2 shows the battery management circuitry 84 disclosed in the '943 Publication, which is briefly discussed. Rechargeable battery 36*r* may comprise a Li-ion polymer battery, which when fully charged can provide a voltage, Vbat(r), of about Vmax(r)=4.2 Volts. However, other rechargeable battery chemistries could be used for battery 36*r* as well.

As noted, an external charger 90, typically a hand-held, battery-powered device, produces a magnetic non-data-modulated charging field 98 (e.g., 80 kHz) from a coil 92. The magnetic field 98 is met in the IPG 10 by front-end charging circuitry 96, where it induces a current in the charging coil 44 in the IPG 10. This induced current is rectified 46 to a voltage V1, which is then filtered (by a capacitor) and limited in its magnitude (by a Zener diode, e.g., to 5.5V), and passed through a back-flow-prevention diode 48 to produce a DC voltage, Vdc. Transistors 102 coupled to the charging coil 44 can be controlled by the IPG 10 (via control signal LSK) to transmit data back to the external charger 90 during production of the magnetic field 98 via Load Shift Keying, as is well known.

As discussed in the '943 Publication, Vdc is provided to battery management circuitry 84, which may reside on an Application Specific Integrated Circuit (ASIC) along with other circuitry necessary for IPG 10 operation, including current generation circuitry (used to provide specified currents to selected ones of the electrodes 16); telemetry circuitry (for modulating and demodulating data associated with telemetry coil 42 of FIG. 1B); various measurement and generator circuits; system memory; etc. The front-end charging circuitry 96 and the battery 36*r* typically comprise off-chip (off-ASIC) components, along with other electronics in the IPG 10, such as the telemetry coil 42; various DC-blocking capacitors coupled to the electrodes 16 (not shown); a microcontroller 100, which can communicate with the ASIC (and the battery management circuitry 84) via a digital bus 88; and other components of lesser relevance here. Microcontroller 100 may comprise in one example Part Number MSP430, manufactured by Texas Instruments, which is described in data sheets at http://www.ti.com/lsds/ti/microcontroller/16-bit_msp430/overview.page?DCMP=MCU_other& HQS=msp430, which is incorporated herein by reference. The ASIC may be as described in U.S.

Patent Application Publication 2012/0095529, which is also incorporated herein by reference.

The battery management circuitry 84 in FIG. 2 is comprised of two circuit blocks: charging circuitry 80 for generating a current for charging the battery 36r, and load isolation circuitry 82 for controllably connecting or disconnecting the battery 36r from the load 75 that the battery 36r powers during normal operation of the IPG 10. Load 75 can comprise both on-chip (on-ASIC) circuit blocks such as the current generation circuitry and the telemetry circuitry mentioned earlier, and off-chip (off-ASIC) components such as the microcontroller 100.

As depicted, the charging circuitry 80, the load isolation circuitry 82, and the battery 36r generally have a T-shaped topology, with the charging circuitry 80 intervening between the front-end charging circuitry 96 (Vdc) and the positive terminal (Vbat(r)) of the battery 36r, and with the load isolation circuitry 82 intervening between Vbat(r) and the load 75.

As discussed in the '943 Publication, the load isolation circuitry 82 can prohibit the battery 36r (Vbat(r)) from being passed to power the load (Vload) dependent on a number of conditions. For example, if the load 75 is drawing a significantly high current (as indicated by overcurrent detection circuitry 74 via assertion of control signal OI); if Vbat(r) is too low (as indicated by rechargeable battery undervoltage detector 70 via assertion of a rechargeable battery undervoltage control signal UV(r)); or if an external magnetic field signal μ is indicated by a Reed switch 78 (e.g., in an emergency condition warranting presentation by the patient of an external shut-off magnet), the load 75 will be decoupled from Vbat(r) via switches 62 or 64. Load isolation circuitry 82 is discussed in further detail in the above-incorporated '943 Publication. Discharge circuitry 68 is also provided to intentionally drain the battery 36r if Vbat(r) is too high.

The charging circuitry 80 begins at Vdc—the DC-voltage produced by the front-end charging circuitry 96 in response to the external charger 90's magnetic field 98. Vdc splits into two paths in the charging circuitry 80 that are connected in parallel between Vdc and Vbat(r): a trickle charging path, and an active charging path, either of which can be used to provide a charging current (Ibat) to the battery 36r.

The trickle charging path is passive, i.e., its operation is not controlled by control signals, and requires no power other than that provided by Vdc to produce a charging current (Itrickle) for the battery 36r. As shown, the trickle charging path presents Vdc to a current-limiting resistor 50 and one or more diodes 52, and is used to provide a small charging current, Itrickle, to the battery 36r. Using a small trickle charging current is particularly useful when the battery 36r is significantly depleted, i.e., if Vbat(r) is below a threshold Vt1, such as 2.7V for example.

To produce Itrickle, Vdc must be higher than the sum of the voltage drops across the resistor 50 and diode(s) 52 and the voltage of the battery 36r, Vbat(r). If Vdc is small (perhaps because the coupling between the external charger 90 and the IPG 10 is poor) or non-existent, diodes 52 will prevent the battery 36r from draining backwards through the trickle charging path. Itrickle is generally on the order of ten milliamps. This is desirably small, because a significantly depleted rechargeable battery 36r can be damaged if it receives charging currents (Ibat) that are too high, as is well known.

The active charging path proceeds in FIG. 2 from Vdc to the battery 36r through a current/voltage source 56, which is used to produce charging current Iactive. In the example of FIG. 2, the active charging path also passes through control and protective measures for the battery management circuitry 84, including a charging current sense resistor 58 used in conjunction with a charging current detector 72, and an overvoltage protection switch 60 used in conjunction with an overvoltage detector 66 to open circuit the active charging path if the battery voltage, Vbat(r), exceeds a maximum value (such as Vmax(r)=4.2V).

Circuitry for the current/voltage source 56 in the active charging path is shown in FIG. 3A. As its name implies, source 56 can be controlled to provide either a constant current or a constant voltage to the battery 36r during active charging. The source 56 comprises a current mirror comprised of P-channel transistors 104 and 106, which receive Vdc and a reference current, Iref, provided by a current source 110 in reference current generator circuitry 113. Current mirror control transistor 104 mirrors a representation of Iref in current mirror output transistor(s) 106 to produce the active charging current, Iactive. In the example shown, M output transistors 106 are wired in parallel, and thus the current provided by output transistor(s) 106 equals Iactive=M*Iref. A single wider output transistor 106 (M times wider than the current mirror control transistor 104) could also be used.

The current source 110 used to produce Iref is adjustable via control signals Itrim[2:0], and also comprises a current mirror. As shown, a system reference current, I' (e.g., 100 nA), is mirrored transistors 116, 118, and 120, each of which are coupled in series to gating transistors controlled by the Itrim control signals. Transistors 116, 118, and 120 are preferably of different widths, or comprise different numbers of transistors in parallel, to provide different contributions to Iref. For example, transistors 116, 118, and 120 may respectively contribute I'*N, I'*2N, and I'*4N to Iref, thus allowing Iref to vary from I'*N to I'*7N in increments of I'*N, depending on which control signals Itrim0, Itrim1, and Itrim2 are active. Additional Itrim control signals and additional current mirror output transistors (e.g., 116-120) could be used to control Iref over a wider range, and/or with smaller resolution. Adjusting Iref in this manner in turn adjusts Iactive via operation of the current mirror transistor 104 and 106 discussed above.

Control signals Itrim are issued by a source controller 86. As shown at the bottom of FIG. 3A, the source controller 86 communicates with the microcontroller 100 by a digital bus 88, and so the microcontroller 100 can control the source controller 86 to in turn control the source 56 via Itrim and other control signals discussed further below.

The mode in which the source 56 operates to generate a charging current depends on the magnitude of the battery voltage, Vbat(r), which is known to the microcontroller 100. If the battery 36r is significantly depleted, i.e., Vbat(r)<Vt1 (e.g., 2.7), the microcontroller 100 commands the source controller 86 to disable the source 56. This occurs by the source controller 86 issuing charge enable control signal Ch_en='0' to the reference current generator 113, which turns off N-channel transistor 108 and disables generation of the reference current, Iref, and hence Iactive. Thus, the battery 36r in this circumstance can only be charged via the trickle charging path, and only if magnetic field 98 and Vdc are present and sufficient.

If Vbat(r)>Vt1, but below an upper threshold Vt2 described further below (i.e., if Vt1<Vbat(r)<Vt2), the source 56 operates in a constant current mode. In this mode, Ch_en='1', and transistor 108 allows Iref and hence Iactive to flow with a magnitude ultimately set by the Itrim control signals. When source 56 operates in constant current mode, Iactive is generally on the order of 50 milliamps. A P-channel transistor 114 in the active current path is fully on in constant current mode, thus allowing Iactive to flow to the battery 36r without resistance.

If Vbat(r)>Vt2 (e.g., 4.0 V), the source 56 operates in a constant voltage mode. Ch_en and the Itrim control signals are still asserted in this mode. Crossing of the Vt2 threshold and switching of charging modes is affected via rechargeable voltage measurement circuitry 111 in the source 56. Vbat(r) is determined in this circuitry 111 via a high-impedance resistor ladder, which produces a voltage Va indicative of Vbat(r). Va and a known band-gap reference voltage, Vref (a), are compared at a comparator 112. When Va>Vref(a), indicating that Vbat(r)>Vt2, the comparator 112 starts to turn off transistor 114, and the source 56 operates in constant voltage mode, providing an essentially constant voltage to the positive terminal of the battery 36r. As the internal cell voltage of the battery 36r increases in this mode, its internal resistance causes Iactive to fall off exponentially, until Vbat(r) reaches a maximum value, Vmax(r) (e.g., 4.2V). At this point, the microcontroller 100 will consider charging of the battery 36r to be complete, and will once again assert Ch_en='0' to curtail further active charging. (Additionally, overvoltage switch 60 may also be opened). By contrast, when Va<Vref(a), indicating that Vbat(r)<Vt2, the comparator 112 turns on P-channel transistor 114, and the source 56 operates in constant current mode as described earlier. Voltage Va can be trimmed as necessary using control signals Vtrim to trim the resistance in the ladder, which essentially sets threshold Vt2.

FIG. 3B generally illustrates operation of the charging circuitry 80 to produce the charging current (Ibat) received by a severely depleted battery 36r (i.e., where Vbat(r) is below an even lower threshold Vuv(r)=2.0V) as a function of time during a charging session, including the trickle, constant current, and constant voltage modes enabled by the charging circuitry 80 as described above. Also shown are typical values for the charging current in each of these modes, and the capacity of the battery 36r illustrated as a percentage.

The battery management circuitry 84 of FIG. 2 provides additional safeguards as discussed in the '943 Publication. For example, diode(s) 54, preferably matching diode(s) 52 in number, are connected between the trickle and active charging paths, which ensure that both the source and drain of the overvoltage switch 60 are biased to the same voltage—to Vbat(r)—even when Vbat(r) is low. Diode(s) 54 thus protect the battery 36r from inadvertently discharging through overvoltage switch 60, particularly at the inopportune time when Vbat(r) is already low, and when it therefore might be difficult to provide a suitably high voltage to the gate of P-channel transistor 60 to turn it off.

The problem of low levels for Vbat(r) is significant. If Vbat(r) is severely depleted, i.e., if Vbat(r)<Vuv(r)=2.0V for example, it may be difficult to recover (recharge) the battery 36r by traditional charging techniques. This is because rechargeable batteries are unable to handle large charging currents without damage, and Itrickle, as passively set by the resistance R of the components (50, 52) in the trickle charging path, may be too large when Vbat(r)<Vuv(r). This problem is exacerbated the lower Vbat(r) becomes.

As discussed above, one solution to the problem of battery depletion is to decouple the battery 36r from the load 75 via the load isolation circuitry 82 to prevent the battery from being further depleted by the load. This is the function of the rechargeable battery undervoltage detector 70, which as disclosed in the '943 Publication is shown in FIG. 4. Note that the rechargeable battery undervoltage detector 70 receives no control signals and thus passively outputs a rechargeable battery undervoltage control signal UV(r), which is preferred because this circuit must work reliably at low levels for Vbat(r) when control signals may not be trustworthy. When Vbat(r)>Vuv(r), the voltage divider formed by diodes 122 and resistor 124 forms a suitably high voltage at the gate of N-channel transistor 128 to turn it on, which pulls UV(r) to '0'. By contrast, when Vbat(r)<Vuv(r), the voltage at the gate of transistor 128 is not high enough to turn on that transistor. UV(r) is thus pulled to '1' (i.e., to Vbat(r)) through a pull-up resistor 126. Both of resistors 124 and 126 are in the range of tens of M-ohms. The forward drop across the diode(s) 122 (as well as their number) and the resistor 124 effectively operate to set the value of threshold Vuv(r). Although not shown, control signal UV(r) may be buffered at the output of the rechargeable battery undervoltage detector 70 to improve its integrity. When UV(r)='1' during a rechargeable battery undervoltage condition, both of the P-channel load isolation switches 62 and 64 (FIG. 2) are off, thus isolating the battery 36r and preventing further depletion.

However, decoupling the battery from the load 75 during a rechargeable battery undervoltage condition brings other problems. The load 75 includes all of the remaining circuitry in the IPG, including the microcontroller 100 and the ASIC, which are completely shut down. Once power is eventually restored to these circuits, their state may be uncertain. For example, the inventors consider it particularly unfortunate that the timing (clock) circuitry in the IPG can lose its time basis, such that when the timing circuitry is later powered (assuming the battery 36r is eventually recharged), the timing circuitry will be reset to zero. Because various data is logged and stored with timestamps for later review, having an unreliable timestamp makes it difficult to review data spanning such a loss of time basis. See, e.g., U.S. Pat. No. 8,065,019 (discussing a solution to this problem involving time basis resetting in the IPG using timestamps provided wirelessly by an external device).

Plus, it may simply be difficult to reliably decouple the load 75 using the load isolation switches 62 and 64 if Vbat(r) is very low (e.g., <1.0 V). This is because the load switches 62 and 64 comprise P-channel transistors, which require a high signal ('1') to turn these transistors off. However, if Vbat(r) drops to very low levels, it cannot be guaranteed that control signal UV(r) can be generated by the rechargeable battery undervoltage detector 70 (FIG. 4) to a voltage sufficient to turn load isolation switches 62 and 64 off, taking the thresholds of those switches into account. This could cause discharging of the battery through the load isolation switches 62 and 64 and the load 75 at the very time when Vbat(r) is already very low and battery depletion is least desired.

Despite the protections provided in the '943 Publication to keep the battery 36r from depleting to severe levels, such depletion is still possible, and the ability to recovery the battery made more difficult during subsequent charging sessions. Solutions to these problems are disclosed herein.

BRIEF DESCRIPTION OF THE DRAWINGS

FIGS. 1A and 1B show a rechargeable-battery implantable pulse generator (IPG) in plan and cross sectional views, in accordance with the prior art.

FIG. 3A shows circuitry for a current/voltage source in the active current path, while

DETAILED DESCRIPTION

A rechargeable-battery Implantable Medical Device (IMD) such as an IPG is disclosed. The IMD includes a primary (non-rechargeable) battery which can be used as a back up to power critical loads in the IMD (e.g., timing circuitry) when the rechargeable battery is undervoltage and other non-critical loads are thus decoupled from the rechargeable battery. A rechargeable battery undervoltage detector provides at least one rechargeable battery undervoltage control signal to a power supply selector, which is used to set the power supply for the critical loads either to the rechargeable battery voltage when the rechargeable battery is not undervoltage, or to the primary battery voltage when the rechargeable battery is undervoltage. Thus, such critical loads can continue to operate despite the rechargeable battery undervoltage condition. Circuitry for detecting the rechargeable battery undervoltage condition may be included as part of the critical loads, and so the undervoltage control signal(s) is reliably generated in a manner to additionally decouple the rechargeable battery from the load to prevent further rechargeable battery depletion. In a modification, an additional primary battery undervoltage detector is provided to generate at least one primary battery undervoltage control signal, and to control the power supply selector to set the power supply for the critical loads to the voltage of the rechargeable battery, even if it is not as high as desired, during a primary battery undervoltage condition.

Figure 2:
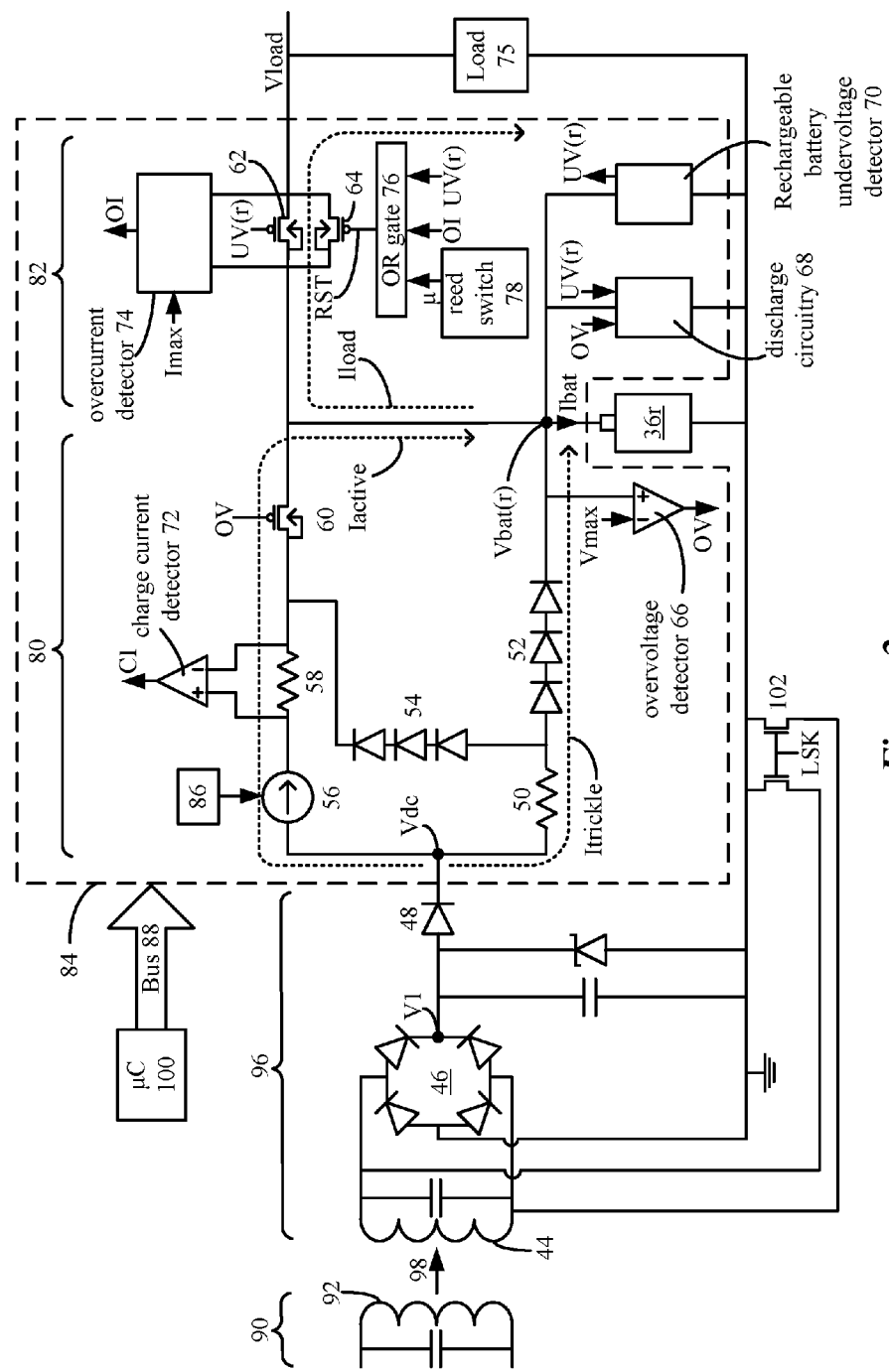
FIG. 2 shows battery management circuitry for an IPG including both trickle and active charging paths, in accordance with the prior art.
Figure 3A:
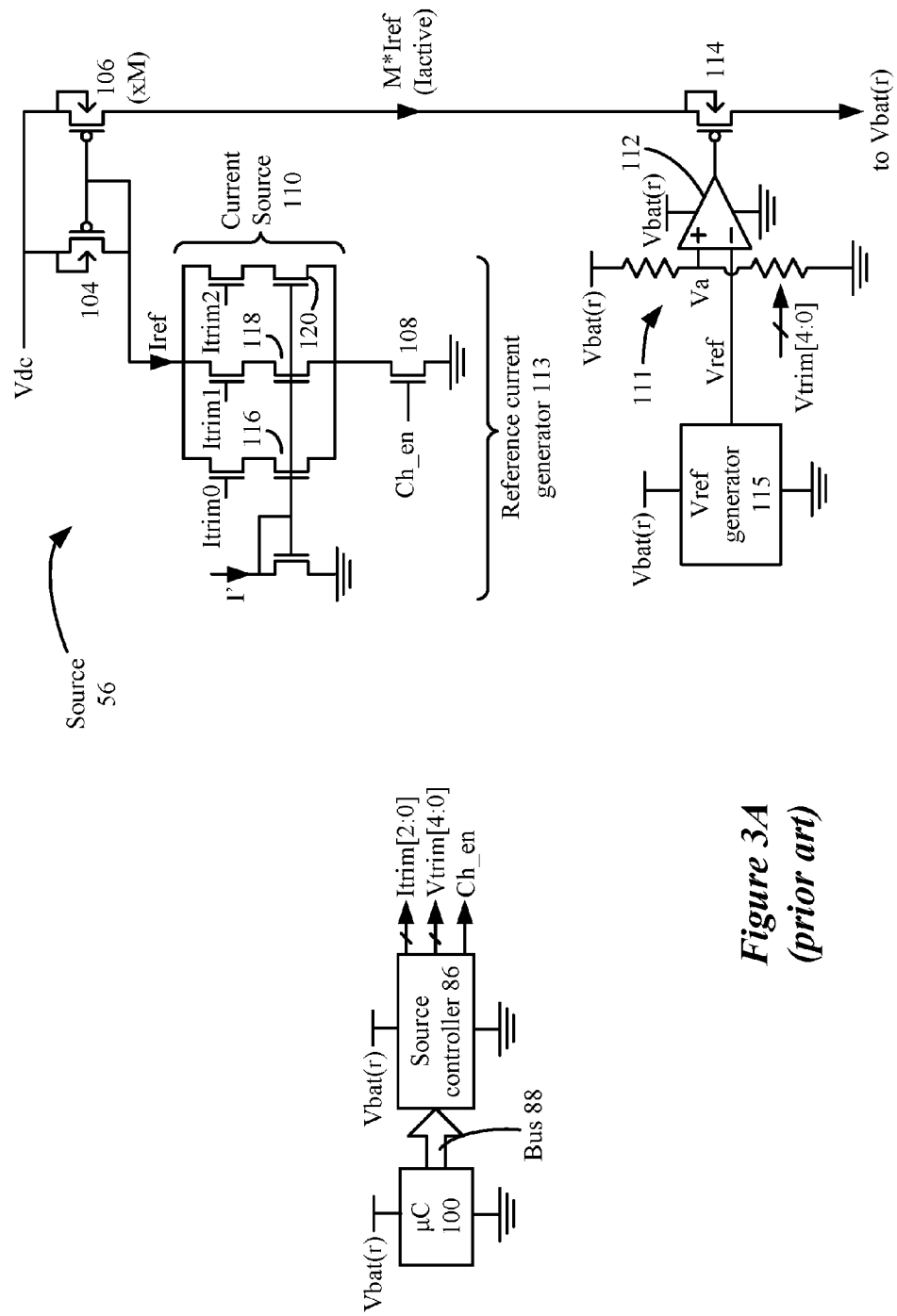
Figure 5A:
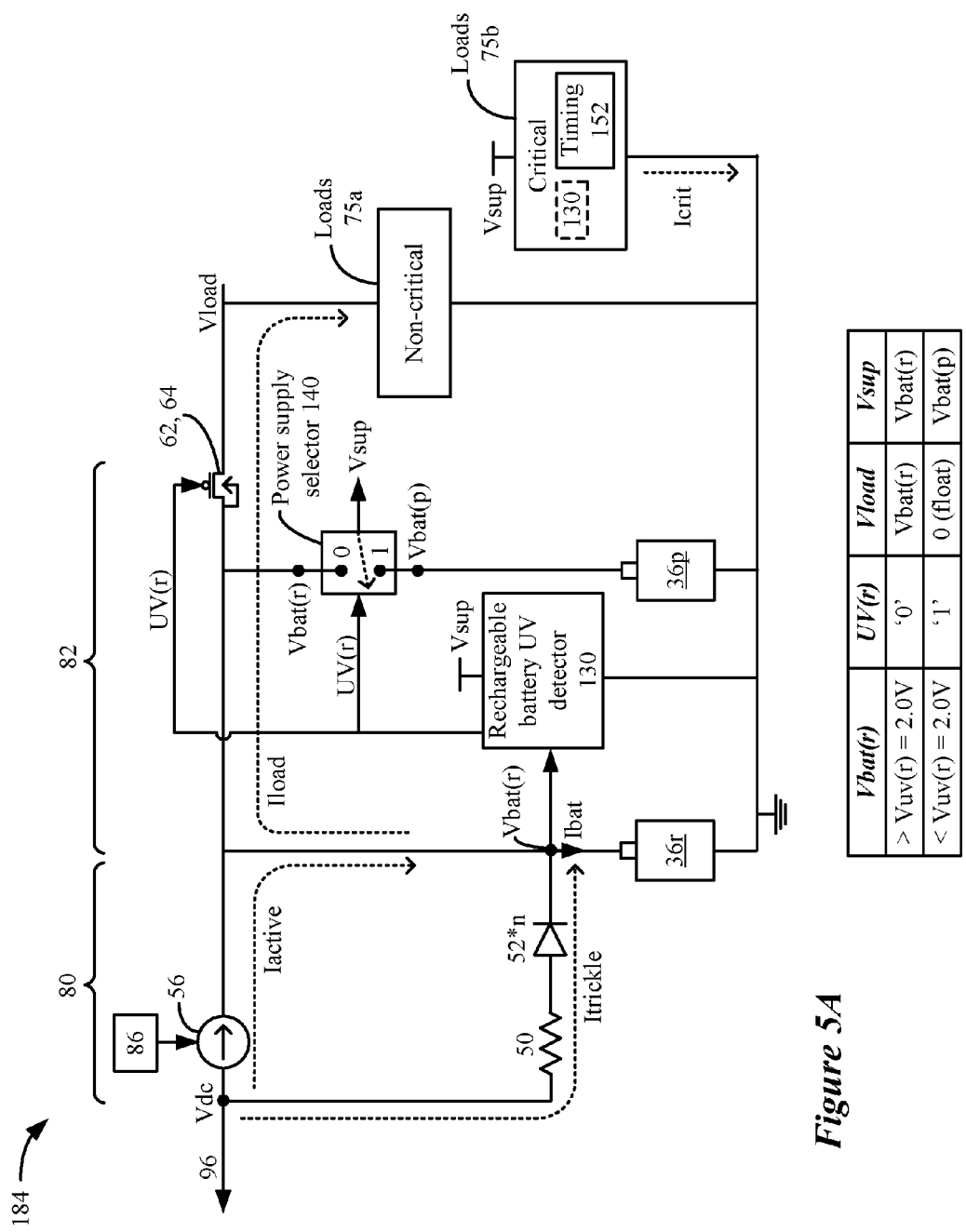
FIG. 5A shows improved battery management circuitry for an IPG having a rechargeable battery and a primary battery, including circuitry for actively detecting an undervoltage condition of the rechargeable battery, and a power supply selector for choosing either the rechargeable or primary battery voltage as a power supply for critical circuitry in the IPG, in accordance with an embodiment of the invention.

FIG. 5A shows improved battery management circuitry 184 for an implantable medical device (IMD) such as an IPG 10 having a rechargeable battery 36r. Many of the components in the battery management circuitry 184 are unchanged from the '943 Publication discussed earlier and shown in FIG. 2, and are thus not described again. Some components (the external charger 90; the front-end charging circuitry 96) have been removed in FIG. 5A for easier viewing, while others have been drawn more simply. Load isolation switches 62 and 64 (FIG. 2) are shown for simplicity as a single transistor, which it could be in an actual implementation, and without control based on overcurrent (OI) or magnetic field ($\mu$) conditions, although such control could also be used. The rechargeable battery 36r may be as described earlier, with a maximum Vbat(r) of Vmax(r)=4.2V. Charging circuitry 80 can remain unchanged to allow the rechargeable battery 36r to be recharged as before.

New to the battery management circuitry 184 is the addition of a primary (non-rechargeable) battery 36p, which is used in conjunction with the rechargeable battery 36r. The primary battery 36p can comprise any number of battery chemistries used in implantable medical devices. The maximum voltage of the primary battery, Vmax(p), when fresh, can be established in different manners, and may comprise a number of cells connected together in series. Vmax(p) is preferably greater than the undervoltage threshold voltage for the rechargeable battery 36r, which as before can be Vuv(r)=2.0V. Still more preferably, Vmax(p) is significantly higher than this threshold Vuv(r), such as from 2.5 to 4.5 V.

Vbat(p) is preferably used to power certain loads in the IPG 10 during a rechargeable battery undervoltage condition—e.g., when Vbat(r)<Vuv(r)=2.0V. In this regard, the load in the IPG has been split into critical loads (load 75b) potentially powered by either the rechargeable battery 36r or the primary battery 36p, as explained further below; and non-critical loads 75a which are only powered by the rechargeable battery 36r, and which are subject to being decoupled from the rechargeable battery 36r when during a rechargeable battery undervoltage condition. Critical loads 75b can include circuitry that is desirable to power even during a rechargeable battery undervoltage condition, such as timing circuitry 152 for example, as well as circuitry used to determine whether the rechargeable battery undervoltage condition exists, such as a rechargeable battery undervoltage detector 130, explained further below. Non-critical loads 75a can comprise circuitry involved in providing therapy to a patient, such as the microcontroller 100 and/or the ASIC mentioned earlier. It is preferable that critical loads 75b in the IPG 10 are limited to reduce the current drawn from the primary battery 36p during a rechargeable battery undervoltage condition (Icrit).

Figure 4:
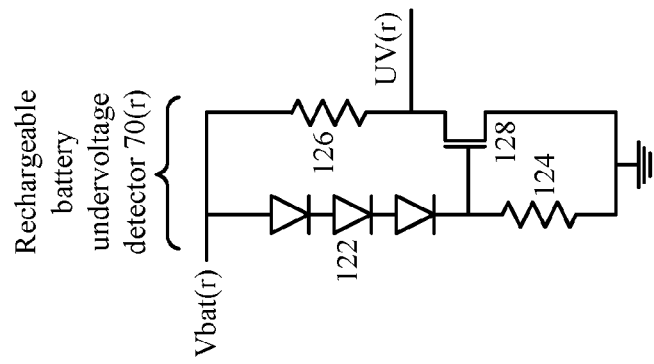
FIG. 4 shows circuitry for passively detecting an undervoltage condition of the rechargeable battery, in accordance with the prior art.
Figure 3B:
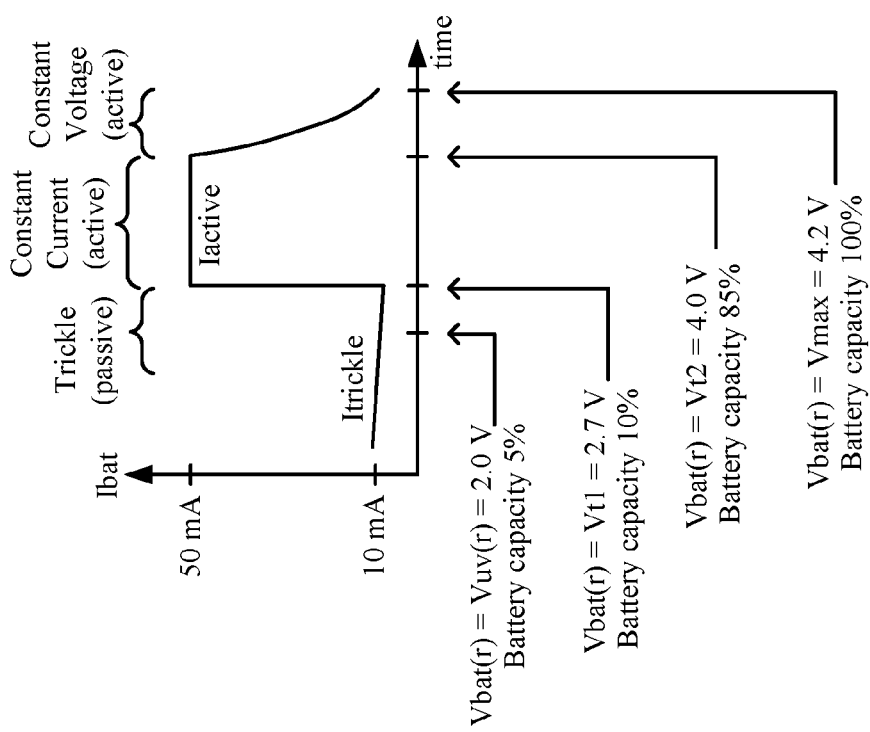
FIG. 3B shows a graph of the battery charging current provided by both the trickle and active charging paths as a function of time, in accordance with the prior art.

Also new to battery management circuitry 184 are the rechargeable battery undervoltage detector 130 just mentioned, and a power supply selector 140. Rechargeable battery undervoltage detector 130 which may differ in construction from the rechargeable battery undervoltage detector 70 described earlier (FIG. 4), but similarly issues a rechargeable battery undervoltage control signal UV(r)='1' when Vbat(r)<Vuv(r), and '0' when Vbat(r)>Vuv(r). Power supply selector 140 passes either Vbat(r) from the rechargeable battery 36r or Vbat(p) from the primary battery 36p as a power supply, Vsup, used by the critical loads 75b. Which of these voltages is selected for Vsup depends on the UV(r) control signal provided by the rechargeable battery undervoltage detector 130.

By way of summary, and as shown in the chart at the bottom of FIG. 5A, when Vbat(r)>Vuv(r), no rechargeable battery undervoltage condition exists. Rechargeable battery undervoltage detector 130 thus sets UV(r)='0', which sets Vsup=Vbat(r) in the power supply selector 140. As such, critical loads 75b are powered by Vbat(r). Because UV(r)='0', P-channel load isolation switches 62 and 64 are on, and thus the non-critical loads 75a are coupled to the rechargeable battery 36r, i.e., Vload=Vbat(r). In effect, when the rechargeable battery 36r is not undervoltage, both loads 75a and 75b are powered by the rechargeable battery 36r (Vbat(r)).

By contrast, when Vbat(r)<Vuv(r), a rechargeable battery undervoltage condition exists. Rechargeable battery undervoltage detector 130 thus sets UV(r)='1', which sets Vsup=Vbat(p) in the power supply selector 140. As such, critical loads 75b are powered by Vbat(p). Because UV(r)='1', load isolation switches 62 and 64 are off, and thus the non-critical loads 75a are decoupled from the rechargeable battery 36r, i.e., Vload=0. (Because Vload isn't actually tied to ground, it will more accurately float, eventually near ground). In effect, when the rechargeable battery 36r is undervoltage, critical loads 75b are powered by the primary battery 36p (Vbat(p)), and the rechargeable battery 36r is decoupled from all loads 75a or 75b, thus preventing depletion of the rechargeable battery 36r.

Figure 5B:
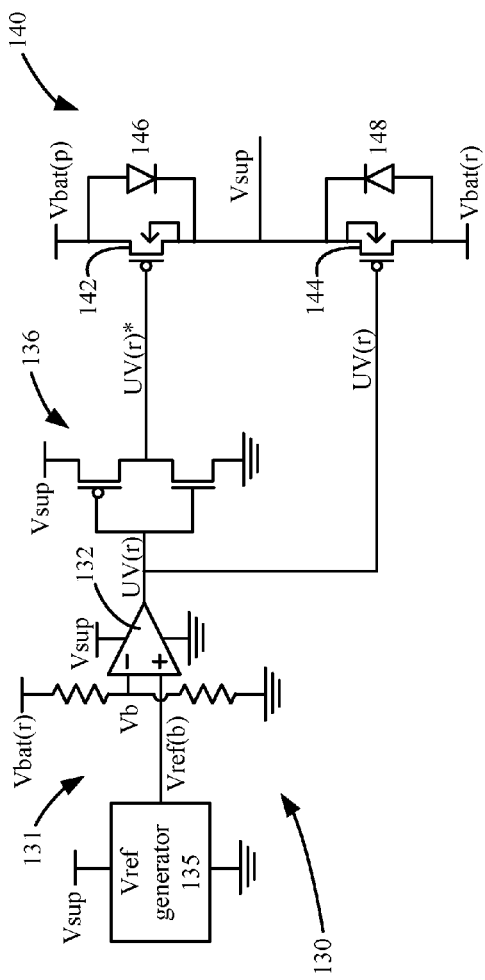
FIGS. 5B and 5C show circuitry details for the active rechargeable battery undervoltage detector and the power supply selector of FIG. 5A, in accordance with embodiments of the invention.

Details of rechargeable battery undervoltage detector 130 and power supply selector 140 are shown in one example in FIG. 5B. It is preferred that rechargeable battery undervoltage detector 130, unlike 70 (FIG. 4), be actively driven to produce at least one UV(r) control signal. Thus, undervoltage detector is powered by Vsup, i.e., by Vbat(r) when sufficient, or by Vbat(p) otherwise. Rechargeable battery undervoltage detector 130 is thus powered as are other critical loads 75b, and may be considered as part of such loads 75b, as shown by the dotted-line box in FIG. 5A.

In the example shown in FIG. 5B, rechargeable battery undervoltage detector 130 includes rechargeable battery measurement circuitry 131, such as a high-impedance resistor ladder, which produces a voltage Vb indicative of Vbat(r). A reference voltage generator 135 generates a known band-gap reference voltage, Vref(b), and Vb and Vref(b) are compared at a comparator 132. When Vb>Vref(b), indicating that Vbat(r)>Vuv(r), the amplifier 132 outputs UV(r)='0.' An inverter 136 in turn provides UV(r)'s inverse, UV(r)*='1', which inverse of true signal UV(r) is not strictly necessary, but can be useful in the power supply selector 140, as discussed subsequently. By contrast, when Vb<Vref(b), indicating that Vbat(r)<Vuv(r), UV(r)='1' and UV(r)*='0.' The resistors in the resistor ladder effectively set the rechargeable battery undervoltage threshold Vuv(r) relative to the value of Vref(b).

Notice that active elements in the rechargeable battery undervoltage detector 130—the Vref(b) generator 135, the comparator 132, and the inverter 136—are powered by Vsup, which should normally be of a sufficient voltage to reliably drive such elements, i.e., either Vbat(r)>Vuv(r), else Vbat(p), which is also preferably greater than Vuv(r) as noted earlier. Thus, control signals UV(r) and UV(r)* are referenced to (i.e., derived from) Vsup, and thus should also be of sufficient voltage.

Note that sufficiency of the UV(r) control signal(s) is beneficial compared to the prior art, and in particular the passive rechargeable battery undervoltage detector 70 discussed previously (FIG. 4). As discussed, rechargeable battery undervoltage detector 70 may not reliably generate a control signal UV(r)='1' of a sufficiently high voltage to turn off P-channel load isolation switches 62 and 64 during a rechargeable battery undervoltage condition, when Vbat(r)<Vuv(r). This could inadvertently cause the rechargeable battery 36r to deplete through the load 75, thus running the risk of severely depleting the rechargeable battery, perhaps to a point where it can no longer be recovered during a subsequent charging session. By contrast, rechargeable battery undervoltage detector 130, with its suitably-high control signal UV(r)='1' referenced to Vsup, will reliably turn off these load isolation transistors 62 and 64 during a rechargeable battery undervoltage condition, thus completely isolating the rechargeable battery and allowing it to be subsequently recharged without difficulty.

While beneficial, it is not strictly necessary in all implementations that the rechargeable battery undervoltage detector 130 be powered by Vsup like the remainder of the critical loads 75b. Instead, the rechargeable battery undervoltage detector 130 may passively generate the UV(r) control signal(s) (see FIG. 4) for the benefit of the load isolation switches 62 and 64 and the power supply selector 140 used to provide Vsup to the critical loads 75b, which is explained next.

Power supply selector 140 sets the power supply voltage for the critical loads 75b, Vsup, to either Vbat(r) or Vbat(p) using the UV(r) control signal(s) generated by the rechargeable battery undervoltage detector 130. In the example shown, power supply selector 140 comprises two transistors 142 and 144, which in this example are P-channel transistors. Transistors 142 and 144 are coupled at their drains to Vbat(p) of primary battery 36p and Vbat(r) of rechargeable battery 36r respectively, and at their sources to Vsup. If Vbat>Vuv(r) (UV(r)/UV(r)*=0/1), transistor 144 is on, transistor 142 is off, and Vbat(r) is passed to Vsup. If Vbat<Vuv(r) (UV(r)/UV(r)*=1/0), transistor 142 is on, transistor 144 is off, and Vbat(p) is passed to Vsup. Thus, and as discussed earlier, Vsup should normally be of a sufficient voltage to reliably power the critical loads 75b and allow them to continue operating, even when non-critical loads 75a are no longer powered. This allows, in just one example, timing circuitry 152 to continue to track the time basis of the IPG 10 despite the rechargeable battery undervoltage condition. Still other beneficial circuits in the IPG 10 could also similarly be powered by the primary battery 36p as part of the critical loads.

Optional diodes 146 and 148 span the sources and drains of transistors 142 and 144, and are beneficial to smooth transition of Vsup between Vbat(r) and Vbat(p) and to otherwise decouple Vbat(r) and Vbat(p). Operation of transistors 142 and 144 are ideally mutually exclusive, with one being on when the other is off. However, due to parasitics, delays and other non-idealities, transistors 142 and 144 could both be on at the same time for a very short period. This runs the risk of shorting Vbat(r) and Vbat(p) during this very short period, with current flowing from the higher to the lower of these voltages. Likewise, transistors 142 and 144 could both be off at the same time for a very short period, which would run the risk that Vsup is decoupled from both Vbat(r) and Vbat(p), and could therefore drop in value to a point at which it could not reliably drive the critical loads 75b.

Diodes 146 and 148 can be used to address these concerns, and setting of the on resistances of the transistors 142 and 144 can also be helpful. The on resistance of the transistors 142 and 144 can be made to have a significant resistance, such as 100-500 ohms. Diodes 146 and 148 can comprise low-threshold voltages diodes, such as Schottky diodes. So configured, if both transistors 142 and 144 are simultaneously on, the significant resistance of the transistor associated with the lower of Vbat(r) or Vbat(p) will impair an influx of current from the higher voltage supply, which again should be very short in duration. If both transistors 142 and 144 are simultaneously off, current can flow from the higher voltage supply through its associated diode to Vsup to prevent its interruption; the other diode associated with the lower voltage supply would not receive current from the higher voltage supply, because its associated diode would be reversed biased.

Figure 5C:
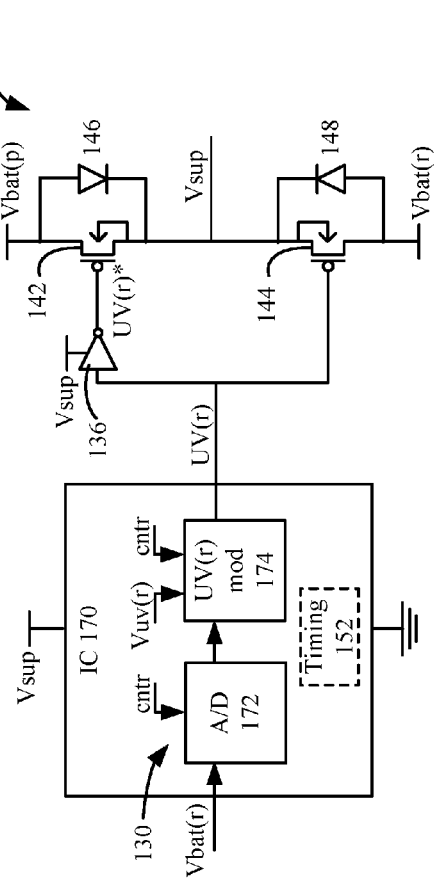

Another manner in which rechargeable battery undervoltage detector 130 can be implemented is shown in FIG. 5C. In this example, rechargeable battery undervoltage detector 130 comprises at least a portion of an integrated circuit (IC) 170 powered by Vsup (as a critical load 75*b*), unlike other integrated circuits (such as microcontroller 100 and/or the ASIC mentioned earlier) that are powered by Vload (as non-critical loads 75*a*). Integrated circuit 170 includes an Analog-to-Digital converter (A/D) 172 that receives Vbat(r), and further includes an undervoltage module 174 for digitally comparing Vbat(r) to the rechargeable battery undervoltage threshold Vuv(r), and for outputting control signal(s) UV(r). In this regard, note that the control signals received by the rechargeable battery undervoltage detector 130 (cntr) can be referenced to (i.e., derived from) Vsup by virtue of their generation within IC 170, which is powered by Vsup. Note also that IC 170 could include other critical loads 75*b*, such as timing circuitry 152 for keeping the IPG 10's time basis.

Figure 6:
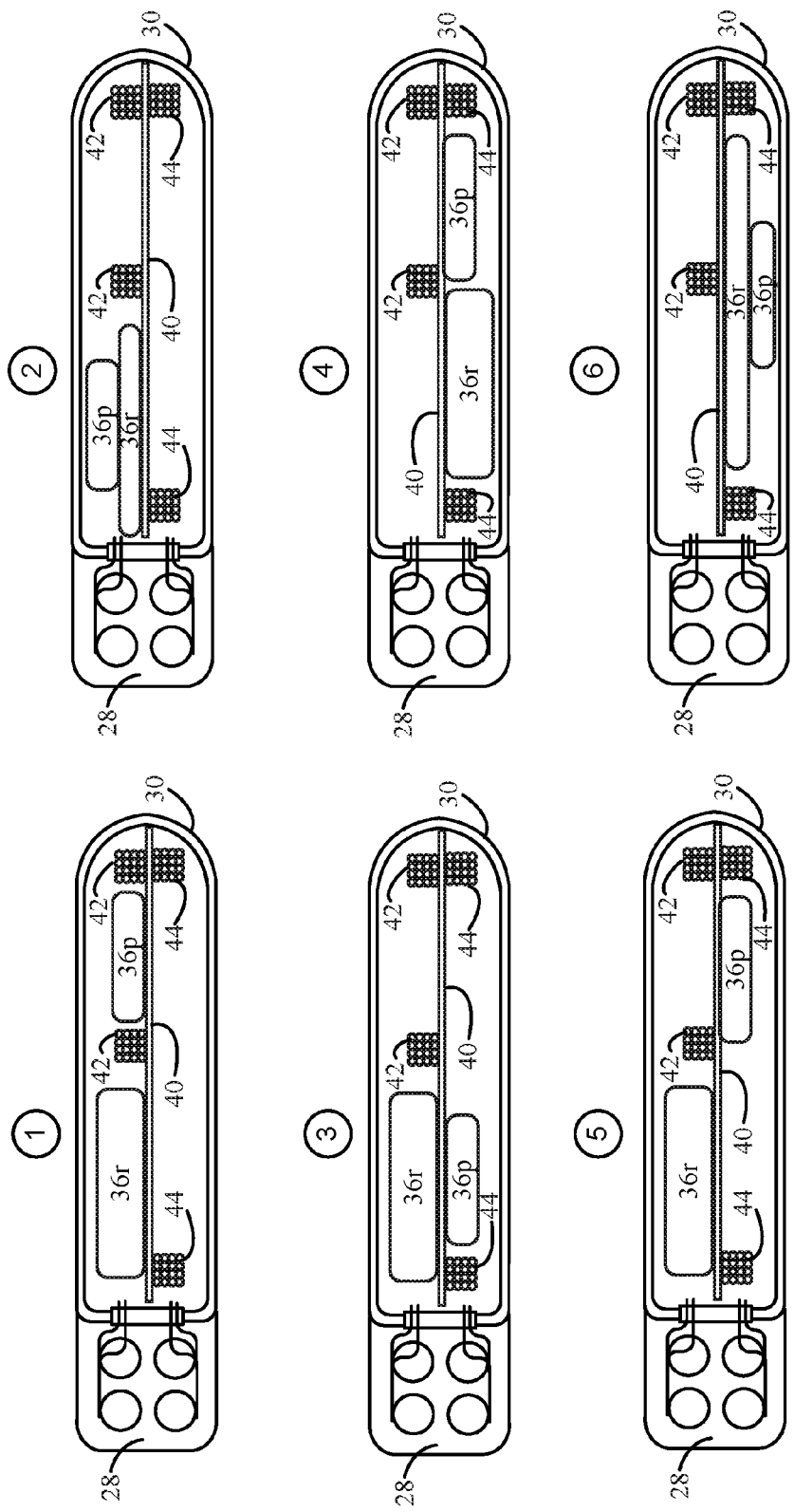
FIG. 6 shows different examples of how the rechargeable battery and primary battery can be configured inside the IPG, in accordance with embodiments of the invention.

FIG. 6 shows different examples of an IPG 10 accommodating both the rechargeable battery 36*r* and the primary battery 36*p*. The batteries 36*r* and 36*p* can be located anywhere inside the IPG 110 so long as they don't impact other IPG functions or interfere unduly with telemetry. Shown are examples in which the batteries 36*r* and 36*p* are side-by-side on one side of the IPG's PCB 40 (4); on opposite sides of the PCB (3, 5); inside the IPG's telemetry coil 42 (1); outside of the IPG's charging coil 44 (1, 2); outside of both coils 42 and 44 (2); and stacked on one side of the PCB (2, 6).

In all of the examples, the IPG 10 includes a charging coil 44 for receiving operational power from an external charger 90 (FIG. 2) and for allowing recharging of the rechargeable battery 36*r*. Each also includes a telemetry coil 42 for communicating with an external controller (not shown), although other forms of antennas could be used for this purpose. Telemetry antennas or coils 42 could also be placed in the IPG's header 28 instead of within its case 30. Although not shown, a single coil 42/44 could be provided for performing both telemetry and charging functions, with these functions being (for example) time multiplexed at the single coil.

In most of the examples shown in FIG. 6, the rechargeable 36*r* is larger than the primary battery 36*p*. This is in recognition that the rechargeable battery 36*r* is preferentially used as the main battery for the IPG 10, with the primary battery 36*p* instead being used as a back-up battery when the voltage of the rechargeable battery 36*r* becomes too low (<Vuv(r)) before it is subsequently recharged. As such, the rechargeable battery 36*r* is preferably as large as possible, while the primary battery 36*p* may be relatively small, as it may be infrequently used assuming the rechargeable battery 36*r* is diligently charged at appropriate intervals.

FIG. 6 merely illustrates some examples of IPG 10 containing batteries 36*r* and 36*p*. Such batteries can be placed anywhere in the IPG 10 as its design permits. Various combinations of the depicted examples could be used. The positions of 36*r* and 36*p* could also be swapped. If necessary, a larger IPG case 30 could be used for the IPG 10 to accommodate both batteries 36*r* and 36*p*. More than one rechargeable battery 36*r*, and/or more than one primary battery 36*p*, could also be used, although not depicted. See also U.S. patent application publication 2015/0100108 (disclosing an IPG having a rechargeable and a primary battery).

Because patients are trained to recharge the rechargeable battery 36*r* in the IPG 10 in a manner to keep it from severely depleting, Vbat(r) would hopefully only rarely fall below Vuv(r), and thus primary battery 36*p* would only be used sparingly to continue to power critical loads 75*b*. Moreover, by minimizing the critical loads 75*b*, the current drawn by such loads (Icrit) is preferably kept low. Thus, the primary battery 36*p* should deplete slowly, and hopefully will last the natural lifetime of the IPG 10 before the primary battery 36*p* reaches its End of Life (EOL)—that is, before Vbat(p) falls to a primary battery undervoltage threshold (Vuv(p)) at which it can no longer power the critical loads 75*b*.

Should Vbat(p) fall below this threshold Vuv(p) and is therefore in effect useless, it is preferable that the power supply selector 140 set Vsup to the voltage of the rechargeable battery, Vbat(r), even if Vbat(r) is insufficient: Although Vbat(r) may be insufficient, it may eventually be recharged or recovered to a point where it can power the loads 75*a* and 75*b*, whereas Vbat(p) cannot.

Figure 7A:
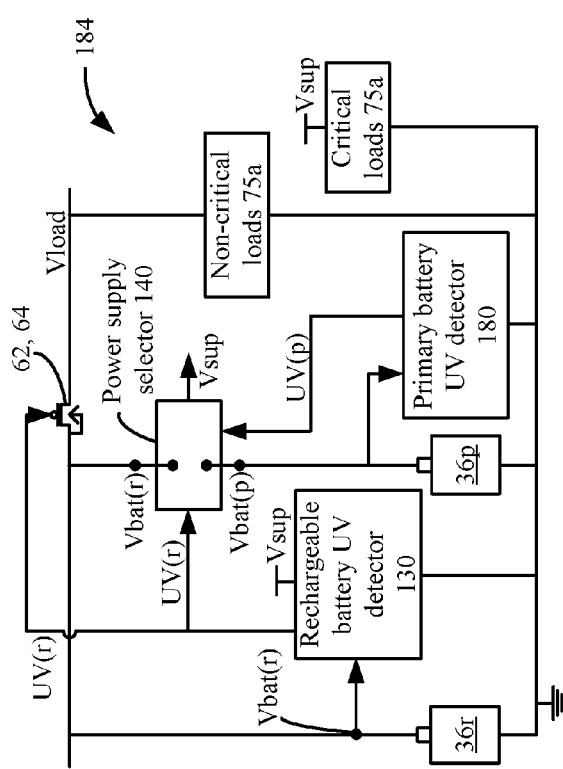
FIGS. 7A and 7B show modification to the improved battery management circuitry of FIG. 5A, which additionally includes a primary battery undervoltage detector for controlling the power supply selector to choose the rechargeable battery voltage during a primary battery undervoltage condition.
Figure 7B:
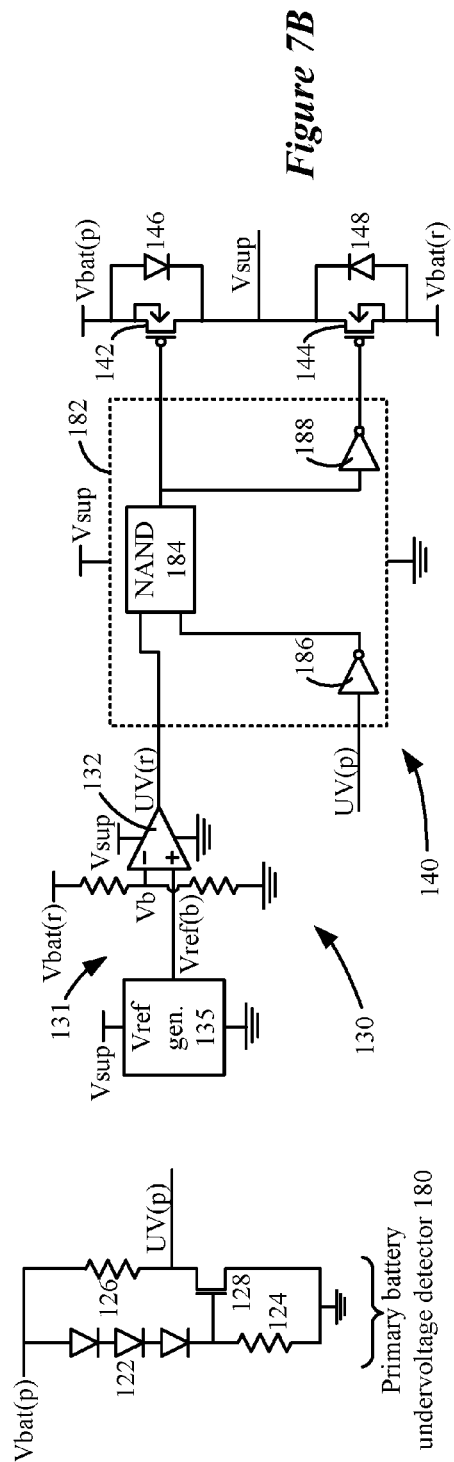

Modification to the battery management circuitry 184 to affect such behavior by the power supply selector 140 is shown in FIGS. 7A and 7B. Included is a primary battery undervoltage detector 180 for outputting a primary battery undervoltage control signal UV(p) indicating when Vbat(p) falls below Vuv(p). In the example shown, Vuv(p)=Vuv(r)=2.0 V, but this is not strictly necessary and different values for these thresholds can be used. Note that both Vuv(r) and Vuv(p) are both preferably set slightly higher than the minimum operating voltage needed to power the critical loads 75*b*.

As shown in FIG. 7B, the primary battery undervoltage detector 180 can be passive, and can comprise the same basic circuitry illustrated for rechargeable battery undervoltage detector 70 described earlier (see FIG. 4), but receiving Vbat(p) at its input. As operation of that circuit 70 was explained earlier, it is not explained again, other than to note that Vuv(p) is set by the diode(s) 122 and the resistor 124.

As shown in FIG. 7B, control signal UV(r) is generated in the rechargeable battery undervoltage detector 130 as before, and is sent to load isolation switches 62 and 64 as before, with a logic level dependent on Vbat(r)'s comparison to Vuv(r). UV(r) is still referenced to Vsup, although Vsup may be set to Vbat(r) regardless of its level, as explained shortly.

Both undervoltage control signals UV(r) and UV(p) are sent to the power supply selector 140, where they are met by a logic block 182 powered by Vsup. Logic gates inside the logic block process UV(r) and UV(p) to produce signals at the gates of the P-channel transistors 142 and 144 to either set Vsup to Vbat(r) or Vbat(p). In the example shown, logic block 182 contains a NAND logic gate 184 and two inverters 186 and 188, although other processing of the UV(r) and UV(b) signals could be used to control power supply selection.

If UV(r)='0', indicating that the rechargeable battery 36*r* is not undervoltage (Vbat(r)>Vuv(r)), the NAND gate outputs a '1', regardless of the level of Vbat(p) or the status of UV(p). The NAND output is provided to the gate of transistor 142, turning it off. This NAND output is inverted 188 ('0') and provided to the gate of transistor 144, turning it on. Thus Vsup=Vbat(r), which is desired because Vbat(r) is sufficient. UV(r)='0' will also turn on load isolation switches 62 and 64, setting Vload=Vbat(r). Thus, both critical loads 75*b* and non-critical loads 75*a* are powered by Vbat(r).

If UV(r)='1', indicating that the rechargeable battery 36*r* is undervoltage (Vbat(r)<Vuv(r)), Vsup will be set to Vbat (p), but only if Vbat(p) is not undervoltage (Vbat(p)>Vuv (p)); else Vsup is set to Vbat(r), even if it is insufficient. This works as follows.

If UV(p)='0', indicating that the primary battery 36p is not undervoltage (Vbat(p)>Vuv(p)), both inputs to the NAND gate 184 are '1' (after UV(p) is inverted 186). The NAND gate 184 outputs a '0', which turns transistor 142 on, and inverter 188 outputs a '1', which turns transistor 144 off. Thus, Vsup=Vbat(p) to power the critical loads 75b, which is desired because Vbat(p) is sufficient. UV(r)='1' will also turn off load isolation switches 62 and 64, decoupling the non-critical loads 75a from Vbat(r) (i.e., Vload=0).

If UV(p)='1', indicating that the primary battery 36p is undervoltage (Vbat(p)<Vuv(p)), inverter 186 inputs a '0' to the NAND gate 184, which will necessarily output a '1', regardless of UV(r). The NAND output is provided to the gate of transistor 142, turning it off, and its inverse is provided to the gate of transistor 144, turning it on. Thus Vsup=Vbat(r) to power the critical loads 75b, even if it is not currently as high as desired. UV(r)='1' will also turn off load isolation switches 62 and 64, decoupling the non-critical loads 75a from Vbat(r) (i.e., Vload=0), although because UV(r) is derived from Vbat(r), it may not be wholly reliable. The table in FIG. 7A summarizes this operation.

The disclosed technique can be used in conjunction with other techniques addressing rechargeable battery depletion in an IMD, such as those disclosed in U.S. Patent Application Publications Serial Nos. 2015/0196768 and 2015/0196764, which are both incorporated herein by reference in their entireties.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
a first battery for providing a first battery voltage;
a second battery for providing a second battery voltage;
a first load powered only by the first battery voltage;
a second load powered by a power supply voltage; and
a power supply selector configured to set the power supply voltage to the first battery voltage or the second battery voltage in accordance with at least the first battery voltage.

2. The device of claim 1, wherein the first battery comprises one of a rechargeable or primary battery, and wherein the second battery comprises the other of the rechargeable or primary battery.

3. The device of claim 1, wherein the first load comprises circuitry involved in providing therapy to a patient.

4. The device of claim 3, wherein the second load comprises timing circuitry.

5. The device of claim 3, wherein the second load comprises measurement circuitry configured to compare the first battery voltage to a threshold.

6. The device of claim 1, wherein the power supply selector is configured to set the power supply voltage to
the first battery voltage if the first battery voltage is above a threshold, and
the second battery voltage if the first battery voltage is below the threshold.

7. The device of claim 1, further comprising at least one switch coupled between the first battery voltage and the first load, wherein
the at least one switch is closed if the first battery voltage is above a threshold, and
the at least one switch is open if the first battery voltage is below the threshold.

8. The device of claim 1, wherein the power supply selector is further configured to set the power supply voltage in accordance with the second battery voltage.

9. The device of claim 8, wherein the power supply selector is configured to set the power supply voltage to
the first battery voltage if the first battery voltage is above a first threshold,
the second battery voltage if the first battery voltage is below the first threshold and if the second battery voltage is above a second threshold, and
the first battery voltage if the second battery voltage is below the second threshold.

10. The device of claim 8, further comprising at least one switch coupled between the first battery voltage and the first load, wherein
the at least one switch is closed if the first battery voltage is above a threshold, and
the at least one switch is open if the first battery voltage is below the threshold.

11. The device of claim 1, wherein the power supply selector comprises a first transistor coupled between the first battery voltage and the power supply voltage and a second transistor coupled between the second battery voltage and the power supply voltage, wherein the first and second transistors are controlled in a mutually exclusive fashion such that one is on when the other is off.

12. The device of claim 1, further comprising
a charging coil configured to receive a magnetic charging field; and
charging circuitry coupled to the charging coil and configured to provide a charging current to the first battery.

13. The device of claim 12, wherein the charging circuitry comprises a first charging path and a second charging path to provide the charging current to the first battery.

14. The device of claim 13, wherein the first charging path passively provides the charging current to the first battery, and wherein the second charging path actively provides the charging current to the first battery.

15. The device of claim 14, wherein the active charging path is activated to provide the charging current only when the first battery voltage exceeds a threshold.

16. An implantable medical device, comprising:
a first battery for providing a first battery voltage;
a second battery for providing a second battery voltage;
a first battery voltage detector configured to determine whether the first battery is undervoltage;
a first load; and
a second load,
wherein if the first battery is not undervoltage,
the first load is powered by the first battery voltage, and
the second load is powered by the first battery voltage, and
wherein if the first battery is undervoltage,
the first load is not powered, and
the second load is powered by the second battery voltage or the first battery voltage.

17. The device of claim 16, wherein the first battery comprises one of a rechargeable or primary battery, and wherein the second battery comprises the other of the rechargeable or primary battery.

18. An implantable medical device, comprising:
a first battery for providing a first battery voltage;
a second battery for providing a second battery voltage;
a first battery voltage detector configured to compare the first battery voltage to a first threshold, and to produce at least one first control signal indicative of the comparison;
at least one switch configured to selectively couple the first battery voltage to a first load in accordance with the at least one first control signal; and
a power supply selector configured to set a power supply voltage to the first battery voltage or the second battery voltage in accordance with at least the at least one first control signal, wherein the power supply voltage powers a second load.

19. The device of claim 18, wherein the first battery comprises one of a rechargeable or primary battery, and wherein the second battery comprises the other of the rechargeable or primary battery.

* * * * *